(12) United States Patent
Scholten et al.

(10) Patent No.: US 8,354,033 B2
(45) Date of Patent: Jan. 15, 2013

(54) METHOD FOR PRODUCING POROUS MICRONEEDLES AND THEIR USE

(75) Inventors: Dick Scholten, Stuttgart (DE); Julia Cassemeyer, Reutlingen (DE); Michael Stumber, Korntal-Muenchingen (DE); Franz Laermer, Weil Der Stadt (DE); Ando Feyh, Tamm (DE); Christian Maeurer, Aachen (DE)

(73) Assignee: Robert Bosch GmbH, Stuttgart (DE)

( * ) Notice: Subject to any disclaimer, the term of this patent is extended or adjusted under 35 U.S.C. 154(b) by 876 days.

(21) Appl. No.: 12/227,509

(22) PCT Filed: Apr. 27, 2007

(86) PCT No.: PCT/EP2007/054175
§ 371 (c)(1),
(2), (4) Date: Feb. 18, 2009

(87) PCT Pub. No.: WO2007/147671
PCT Pub. Date: Dec. 27, 2007

(65) Prior Publication Data
US 2009/0200262 A1      Aug. 13, 2009

(30) Foreign Application Priority Data
Jun. 23, 2006   (DE) .......................... 10 2006 028 781

(51) Int. Cl.
*B44C 1/22*     (2006.01)
*C25F 3/00*     (2006.01)
(52) U.S. Cl. .................. 216/11; 216/2; 216/56
(58) Field of Classification Search .............. 216/11, 216/56, 2
See application file for complete search history.

(56) References Cited

U.S. PATENT DOCUMENTS

| | | | |
|---|---|---|---|
| 6,334,856 B1 | 1/2002 | Allen et al. | |
| 2002/0193754 A1* | 12/2002 | Cho | 604/272 |
| 2005/0171480 A1* | 8/2005 | Mukerjee et al. | 604/173 |
| 2008/0197106 A1* | 8/2008 | Feyh | 216/2 |

FOREIGN PATENT DOCUMENTS

| | | |
|---|---|---|
| EP | 0 625 285 | 3/2000 |
| JP | 2002-517300 | 6/2002 |
| JP | 2004-507371 | 3/2004 |
| JP | 2004-538106 | 12/2004 |
| WO | WO 00/05339 | 2/2000 |
| WO | WO 02/17985 | 3/2002 |
| WO | WO 02/062202 | 8/2002 |
| WO | WO 2006101459 A1 * | 9/2006 |

OTHER PUBLICATIONS

Jing, Ji et al.: "Microfabricated silicon microneedle array for transdermal drug delivery" Journal of Physics: Conference Series Top Publishing UK, vol. 34, No. 1, 2006, pp. 1127-1131.
Jing, Ji et al.: "Microfabricated microneedle with porous tip for drug delivery," Journal of Micromechanics and Microengineering IOP Publishing UK, vol. 16, No. 5, May 2006, pp. 958-964.

* cited by examiner

*Primary Examiner* — Roberts Culbert
(74) *Attorney, Agent, or Firm* — Kenyon & Kenyon LLP

(57) ABSTRACT

A method for producing porous microneedles (10) situated in an array on a silicon substrate includes: providing a silicon substrate, applying a first etching mask, patterning microneedles using a DRIE process ("deep reactive ion etching"), removing the first etching mask, at least partially porosifying the Si substrate, the porosification beginning on the front side of the Si substrate and a porous reservoir being formed.

12 Claims, 2 Drawing Sheets

US 8,354,033 B2

METHOD FOR PRODUCING POROUS MICRONEEDLES AND THEIR USE

BACKGROUND OF THE INVENTION

1. Field of the Invention

The present invention relates to a method for producing porous microneedles.

2. Description of Related Art

The concept of administering medications, that is, medicinal and biochemical active substances, is being pursued in many variants. There are basically several important criteria which have to be observed in this context. Among others of these important criteria are the mechanical stability and the biocompatibility of the microneedles. At the same time, the production of the microneedles should be based on simple and well-controlled processes, in order to work cost-effectively, particularly at high volume.

Porous silicon is regarded as suitable material that basically satisfies the requirements mentioned. The material demonstrates good compatibility with biochemical substances, and is well able to be removed by the human (or animal) body.

Thus, microneedles are known from U.S. Pat. No. 6,334, 856, for example, which, besides metals, ceramics and polymers also include porous silicon. There are basically two procedures for producing microneedles from porous silicon: Either (a) a silicon substrate is first made porous, and microneedles are subsequently patterned from this by etching, or (b) the substrate is first etched for the formation of microneedles and porosified thereafter. For reasons of process technology, the first procedure is very difficult. Although it is basically suitable for producing porous microneedles, the second procedure (b) requires a production method having specific step sequences, each individual step having a need to be composed of a well manageable individual process, and all the step sequences together should form an advantageous combination of an overall method. In particular, the method should make possible the production of microneedles without a great technical effort, and thereby in a cost-effective manner. Nevertheless, sufficient mechanical stability of the microneedles thus produced has to be ensured. The microneedles produced therefore must have neither brittle nor soft materials, which could, for instance, lead to splinters chipping off.

BRIEF SUMMARY OF THE INVENTION

It is an object of the present invention to provide a method for producing porous microneedles and their use, the method being made up of easily manageable and controllable individual processes, and therefore ensuring a controllable and cost-effective overall method.

The present invention provides the advantage that a method having specific, technical and well manageable individual steps is achieved. The combination and the sequence of these individual steps also ensures technologically completely uncritical transitions between the individual steps. Finally, a cost-effective method is also achieved.

DETAILED DESCRIPTION OF THE INVENTION

Figure 1:
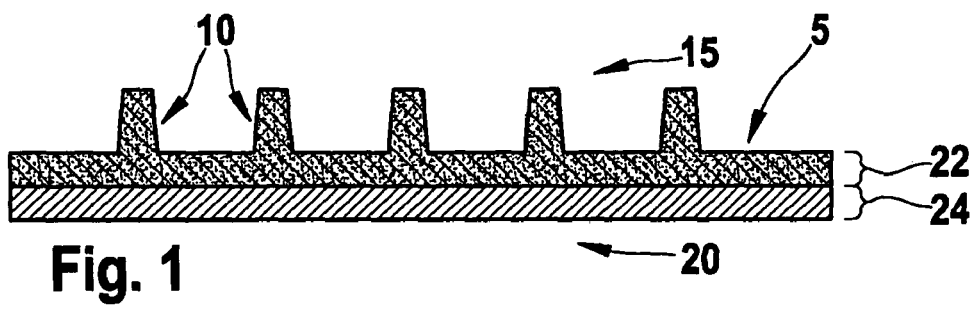
FIG. 1 shows an exemplary embodiment of the present invention having a partially porosified silicon substrate, in a side view.

The basic method for producing porous microneedles 10, for the transdermal administration of medications, is now first explained with the aid of FIG. 1. The method specifically includes this sequence of steps:

providing a silicon substrate 5,
applying a first etching mask,
patterning microneedles 10 using a DRIE process ("deep reactive ion etching"),
removing the first etching mask,
at least partially porosifying Si substrate 5, the porosification beginning on front side 15 of Si substrate 5, and a porous reservoir being formed.

Each process step is based on a technically well manageable and controllable individual process. Working with a silicon substrate 5 is standard in semiconductor technology, and thus there are numerous proven processes which one may immediately fall back upon. This selection also has the advantage of providing a cost-effective starting material.

Applying an etching mask to a silicon substrate 5 also does not call for a critical process step, and may be carried out in numerous variations with respect to masking material or application technique. The application also includes techniques such as plating. As an example, in order to apply an etching mask, first of all a masking layer may be applied to substrate 5 over the whole surface via a CVD process ("chemical vapor deposition") and on top of that, a resist layer via spin-on deposition. After that, the patterning of the later etching mask is specified in the resist layer by a lithography step and a development step, and then this patterning is transferred to the masking layer lying under it, using an etching process. After removal of the resist layer, the etching mask remains for the etching process that is now to follow.

The microneedles are structured using a DRIE process. In this etching process, the so-called "Bosch Process" is preferably carried out, which is known, for example, from EP 0 625 285 B1. Using this deep etching method, deep etched regions, such as grooves, having largely vertical walls, may be produced in the silicon substrate. Deposition steps, during which a teflon-type polymer is deposited on the side wall, and fluorine-based etching steps that are isotropic per se, which are made locally anisotropic by driving forward the side wall polymer during the etching, alternate with each other. In the method according to the present invention, the regions that are not etched are able to form microneedles 10. After their patterning, microneedles 10 are then situated in an array on Si substrate 5.

As soon as microneedles 10 are patterned, the etching mask is removed. The removal of the etching mask may also be accomplished in various ways, depending on the material of the etching mask. One possibility is, for example, removal of the etching mask in an etching solution.

Finally, Si substrate 5 is at least partially porosified. The so-called anodizing process is preferably carried out for the porosification of silicon. In this process, the silicon is etched electrochemically in an HF(hydrofluoric acid)-containing electrolyte while being acted upon by an electric current flow, whereby pores are formed in the silicon. The method according to the present invention in any case provides that the porosification begins on front side 15 of silicon substrate 5. In this document, front side 15 of Si substrate 5 designates the side having microneedles 10, and back side 20 designates the side of silicon substrate 5 opposite to front side 15. Using this procedure, it is ensured that microneedles 10 are porosified in any case, and that, at the same time, a setting or control of the depth of the porous region in substrate 5 itself is made possible. For instance, in FIG. 1, silicon substrate 5 is only porosified so far that next to a first porosified layer 22 a second, non-porosified layer 24 remains in Si substrate 5. During porosification, it is provided that a porous reservoir should also be produced in Si substrate 5. Thereby, porous needles 10 and a porous reservoir are advantageously formed in one process step. In addition, a porous reservoir is integrated in substrate 5 as a result of the method.

We shall now explain various modifications of the method according to the present invention, which have further advantages to offer, depending on the requirements.

Figure 2:
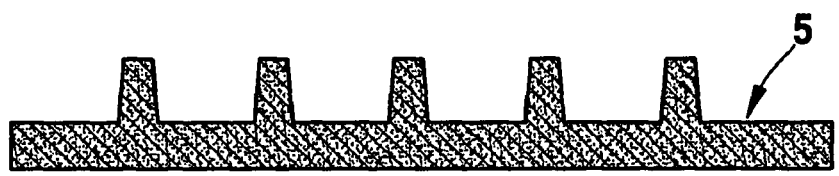
FIG. 2 shows a further exemplary embodiment of the present invention having a completely porosified silicon substrate, in a side view.

In one alternative exemplary embodiment according to FIG. 2, the method may be varied in such a way that Si substrate 5 is completely porosified during the porosification. Because substrate 5 is porosified all the way through to its back side 20, supplying medication is made possible even from back side 20.

Figure 3:
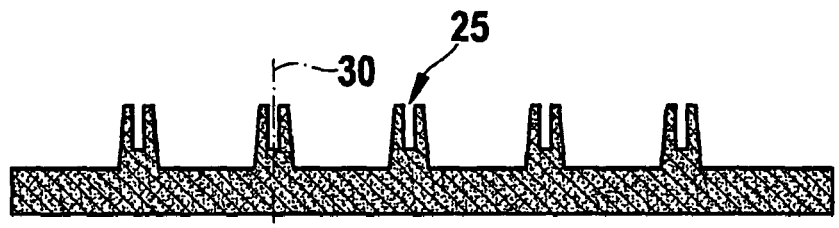
FIG. 3 shows a further exemplary embodiment of the present invention having a passage in the middle of the microneedles, in a side view.

In an additional exemplary embodiment according to FIG. 3, when microneedles 10 are patterned using the DRIE process, an inner passage 25 in microneedles 10 is etched at the same time. The fluid transport inside microneedles 10 is simplified by producing passage 25. In this example, passage 25 is etched in such a way that it runs symmetrically to middle of needle 30.

Figure 4:
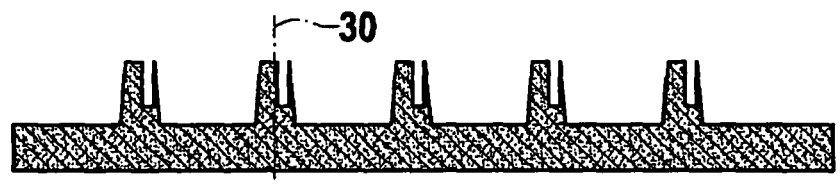
FIG. 4 shows a further exemplary embodiment of the present invention having a passage that is asymmetrical to the middle of the needle, in a side view.

In an additional exemplary embodiment according to FIG. 4, when microneedles 10 are patterned using the DRIE process, an inner passage 25 in microneedles 10 is etched at the same time in such a way that passage 25 runs asymmetrically to middle of needle 30. Because of this lateral offset of passage 25 from middle of needle 30, thinner, that is, sharper edges are created at the tips of the needles. These sharper needles penetrate more easily into a skin that is to be treated.

Figure 5:
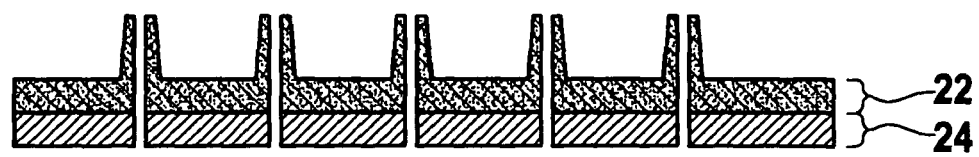
FIG. 5 shows a further exemplary embodiment of the present invention having a passage that extends to the back side of the silicon substrate, in a side view.

In yet another exemplary embodiment according to FIG. 5, as in FIG. 1, a second, non-porosified layer 24 is provided in Si substrate 5. Now, during patterning of microneedles 10, an inner passage 25 is etched in microneedles 10, this passage 25 being continued in second layer 24, made up of non-porosified silicon, all the way to back side 20, using a second DRIE process. The second, additional trench process also permits the supply of medication from back side 20 of Si substrate 5, even when a second layer 24 of non-porosified silicon is present.

Figure 6:
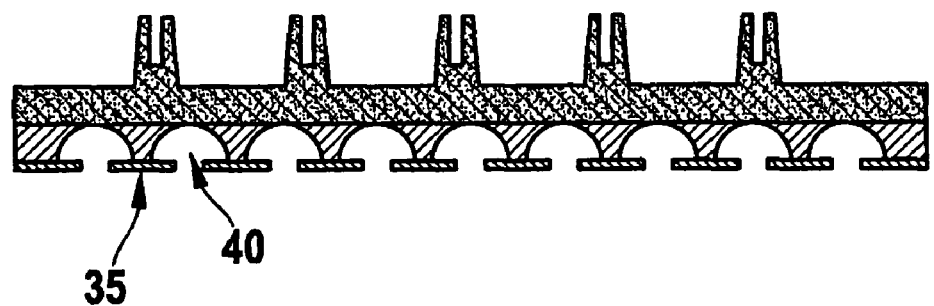
FIG. 6 shows a further exemplary embodiment of the present invention having openings at the back side of the silicon substrate, in a side view.

In still another exemplary embodiment according to FIG. 6, a second, non-porosified layer 24 is also present in Si substrate 5. However, alternatively to FIG. 5, passage 25 is not etched right up to back side 20 of Si substrate 5. Instead, during the patterning of microneedles 10, an inner passage 25 is etched into microneedles 10, first porosified layer 22 being transformed by an isotropic etching process in second, non-porosified layer 24 into a state that is accessible from back side 20 of Si substrate 5. Because of that, first layer 22 is opened at back side 20, point-by-point or from area to area, that is, first layer 22 having the porous reservoir is uncovered at such locations by recesses 40 in second layer 24 at back side 20. Thus, the supply of medication from back side 20 to the porous reservoir is further possible. The isotropic etching process is advantageously implemented, after the partial porosification of Si substrate 5, in an anodizing process having an electric current flow through an electrical polishing process, while reversing the direction of the current, and while using a second etching mask 35 at back side 20 of Si substrate 5. The anodizing process and the electropolishing process are thus simply carried out one after the other in the same electrolyte.

Figure 7:
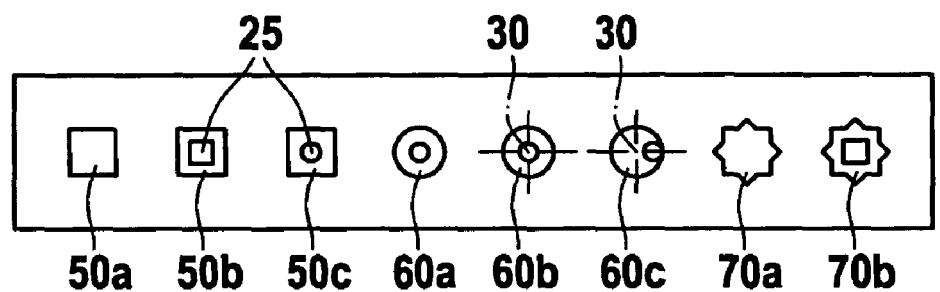
FIG. 7 shows exemplary embodiments of the microneedles in different shapings, in a top view.

FIG. 7 also shows that variously shaped microneedles 10 are able to be patterned, having a square 50a-50c, a circular 60a-60c and/or a star-shaped outline 70a-70b in a top view. One may also recognize different shapes in passages 25 in a top view, in a few examples of so-called hollow needles 50b,50c,60b,60c,70b. So-called solid needles 50a,60a,70a, however, have no inner passages 25. Four-cornered shapes 50a-50c of microneedles 10 are preferably square. In the case of the star-shaped outline, microneedles 10 have several points, in a top view. In the examples in FIG. 7, eight points are present (in the case of microneedles 70a,70b). An inner passage 25 that is present, itself may be square (in microneedles 50b, 70b) or circular (in microneedles 50c, 60b,60c). As was mentioned before, it is also possible to position inner passage 25 symmetrically (as in microneedles 50b,50c,60b, 70b) or asymmetrically (as in microneedle 60c) to middle of needle 30. All these variations may be provided, according to expediency, in any desired combination, in one or in different arrays or substrates 5.

Figure 8:
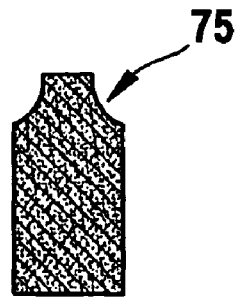
FIG. 8 shows an example embodiment of tapering of the upper region of patterning microneedles.

Finally, it is possible in all method variants, when patterning microneedles 10, to bring about a tapering 75 in the upper region of microneedles 10, as shown in FIG. 8, by specific process management, especially by isotropic etching. This further eases the penetration of microneedles 10 into a skin that is to be treated. Putting a slant on microneedles 10 in the upper region may particularly be carried out by deep etching according to the "Bosch Process" in a controlled manner via the setting of parameters.

Porous microneedles 10, produced by the method explained, are suitable for use in (bio)chemical, medicinal and clinical fields. Thus, these microneedles 10 may further be used for producing an administration unit for medications for the treatment of pain, allergies, infections, cardiovascular diseases and/or cancer.

What is claimed is:
1. A method for producing porous microneedles situated in an array on a silicon substrate, comprising:
   providing a silicon substrate;
   applying a first etching mask on the silicon substrate;
   patterning microneedles using a deep reactive ion etching (DRIE) process;
   removing the first etching mask; and
   porosifying the silicon substrate to a limited extent to form a first porosified layer adjacent to a second, non-porosified layer which remains in the silicon substrate;
   wherein:
      the porosification begins on a front side of the silicon substrate and forms a porous reservoir;
      during the patterning of the microneedles, an inner passage is etched into each microneedle; and the first porosified layer is transformed, by an isotropic etching process in the second, non-porosified layer, into a state that is accessible from a back side of the silicon substrate.

2. The method as recited in claim 1, wherein the inner passages are etched to be asymmetrical to the respective centers of the respective microneedles into which they are etched.

3. The method as recited in claim 1, wherein each of at least one of the inner passages is etched asymmetrically to the middle of the respective needle.

4. The method as recited in claim 1, wherein the inner passages are extended through the second, non-porosified layer to a back side of the silicon substrate using a second DRIE process.

5. The method as recited in claim 4, wherein the microneedles are patterned to have at least one of a square shape, a circular shape and a star shape when viewed from the top.

6. The method as recited in claim 4, wherein, during the patterning of the microneedles, a tapering is effected in the upper region of each microneedle by isotropic etching.

7. The method as recited in claim 4, wherein the microneedles are configured for application of medications.

8. The method as recited in claim 1, wherein the isotropic etching process is implemented, after the partial porosification of the silicon substrate, in an anodizing process having an electric current flow through an electrical polishing process, while reversing the direction of the current, and while using a second etching mask at the back side of the silicon substrate.

9. The method as recited in claim 1, wherein the inner passages of the microneedles are etched at the same time.

10. The method as recited in claim 1, wherein the microneedles are patterned to have at least one of a square shape, a circular shape and a star shape when viewed from the top.

11. The method as recited in claim 1, wherein, during the patterning of the microneedles, a tapering is effected in the upper region of each microneedle by isotropic etching.

12. The method as recited in claim 1, wherein the microneedles are configured for application of medications.

* * * * *

UNITED STATES PATENT AND TRADEMARK OFFICE
CERTIFICATE OF CORRECTION

PATENT NO. : 8,354,033 B2
APPLICATION NO. : 12/227509
DATED : January 15, 2013
INVENTOR(S) : Scholten et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 930 days.

Signed and Sealed this
First Day of September, 2015

Michelle K. Lee
*Director of the United States Patent and Trademark Office*